United States Patent [19]

Küpper et al.

[11] Patent Number: 5,284,982
[45] Date of Patent: Feb. 8, 1994

[54] METHOD FOR THE CYCLOOLIGOMERIZATION OF 3-HYDROXY-1 ALKYNES

[75] Inventors: Friedrich-Wilhelm Küpper, Marl; Wolfgang Schröder; Heinz-Werner Voges, both of Dorsten, all of Fed. Rep. of Germany

[73] Assignee: Huels Aktiengesellschaft, Marl, Fed. Rep. of Germany

[21] Appl. No.: 13,375

[22] Filed: Feb. 4, 1993

[30] Foreign Application Priority Data

Feb. 20, 1992 [DE] Fed. Rep. of Germany ....... 4205115

[51] Int. Cl.$^5$ ............................................. C07C 33/26
[52] U.S. Cl. .................................. 568/811; 568/844; 568/848; 568/902
[58] Field of Search ............... 568/902, 905, 840, 848, 568/811, 844

[56] References Cited

PUBLICATIONS

Chini et al., "J. Chem. Soc. C" [1967] p. 830.

*Primary Examiner*—Werren B. Lone
*Attorney, Agent, or Firm*—Oblon, Spivak, McClelland, Maier & Neustadt

[57] ABSTRACT

The invention relates to a method of cyclooligomerization of 3-hydroxy-1-alkynes having 4–20 C atoms, particularly cyclooligomerization of 3-methyl-1-butyne-3-ol to yield 1,3,5-tris(α-hydroxyisopropyl)-benzene, with the aid of nickel-containing catalysts formed from a nickel compound, a phosphite of an ortho-substituted phenol, and an organoaluminum compound of formula $$AlR_{(3-n)}X_n,$$

where
  R represents alkyl,
  X represents hydrogen or chlorine, and
  n=0 or 1, or an alkyllithium or alkylmagnesium compound, in the presence of
  an aprotic diluent,
  (optionally) an unconjugated diene, and
  (optionally) a portion of the given 3-hydroxy-1-alkyne being oligomerized.

13 Claims, No Drawings

METHOD FOR THE CYCLOOLIGOMERIZATION OF 3-HYDROXY-1 ALKYNES

SUMMARY OF THE INVENTION

The present invention relates to a method for the cyclooligomerization of 3-hydroxy-1-alkynes. More particularly, the invention relates to a method for producing 1,3,5-tris(α-hydroxyisopropyl)-benzene from 3-methyl-1-butyne-3-ol in the presence of carbonyl-free homogeneous nickel-containing catalysts having enhanced activity and which may be obtained from carbonyl-free precursors. These catalysts bring about the cyclooligomerization of 3-hydroxy-1-alkynes with little or no incubation time, and in general and in the case of 3-methyl-1-butyne-3-ol they produce the desired 1,3,5-substituted aromatic trimer with only minimal amounts of the 1,2,4-isomer byproduct. The enhanced activity of the present catalysts enable the use of only very small quantities of catalyst while still accomplishing cyclooligomerization in good yields under mild conditions. In this way, the nickel content of the initially produced cyclooligimer can be reduced substantially, facilitating subsequent purification.

BACKGROUND OF THE INVENTION

It is known that alkynes can be converted to acyclic and cyclic oligomers with the aid of catalysts containing transition metals. As a rule, the catalysts used for producing substituted benzene derivatives by cyclotrimerization of alkynes contain complex compounds of nickel or cobalt.

Cobalt compounds seem to favor the formation of 1,2,4-substituted aromatics from 3-hydroxy-1-alkynes (see Chini et al., *J. Chem. Soc. C*, 1967, 830; and Chukhadzhyan et al., *Zh. Org. Khim.*, 8, 1972, 119; Id., 10, 1974, 1408). When propargyl alcohol is polymerized in the presence of $Ni(CO)_2(P(C_6H_5)_3)_2$, a mixture of 1,3,5- and 1,2,4-tris(hydroxymethyl)-benzene is obtained as well as some difficult-to-remove byproducts in a vigorous reaction (see Reppe et al., *Liebigs Ann.*, 560, 1948, 104).

In Ger. Pat. 1,159,951, carbonyl-free phosphite- and thiophosphite-containing nickel catalysts are described which are suitable for the cyclooligomerization of 3-hydroxy-1-alkynes, e.g., 3-methyl-1-butyne-3-ol. Good yields can be obtained with these catalysts under relatively mild conditions. Particularly good results have been obtained when the aryl phosphite ligands of the catalyst contain voluminous substituents on the aromatic nucleus in the position ortho to the oxygen. A disadvantage of such catalysts is that the nickel-containing precursors subsequently reacted with suitable phosphites to obtain the target catalysts are, e.g., bis(acrylonitrile)-nickel(O), bis(acrolein)-nickel(O), or bis(duroquinone)-nickel(O), and are obtained from highly toxic nickel tetracarbonyl. The same reservation applies to the catalysts described in Ger. Pats. 2,046,200 and 2,056,555, which are produced from $Ni(CO)_4$ and triaryl phosphites, and which are also suitable for, e.g., cyclooligomerization of 3-methyl-1-butyne-3-ol. Since it is desirable to minimize or avoid the use of toxic compounds like $Ni(CO)_4$ in industrial processes in order to make production methods safe and environmentally benign, catalysts made from nickel tetracarbonyl like those described above are disfavored due to their danger.

There are references in the literature to carbonyl-free catalysts for cyclooligomerization of 3-hydroxyalkynes, particularly of 3-methyl-1-butyne-3-ol, but the systems described heretofore still are beset with disadvantages which militate against their use in industrial production. An example is bis(tributylphosphine) nickel(II) halides (see *Gazz. Chim. Ital.*, 103, 1973, 849), of which the most noteworthy representative is $(Bu_3P)_2NiBr_2$ on account of its activity and selectivity in the trimerization of 3-methyl-1-butyne-3-ol. This catalyst displays its catalytic activity only after an incubation time of indeterminate duration in the presence of 3-methyl-1-butyne-3-ol, wherewith after completion of the catalyst formation the 3-methyl-1-butyne-3-ol cyclooligomerizes exothermically, with a rapid rise in temperature which can be controlled only with difficulty. This drawback is in addition to the high cost of the nickel bromide-phosphine complex and the fact that the complex contains a halide which is undesirable. Also, the 1,3,5-tris(α-hydroxyisopropyl)-benzene raw product obtained with this catalyst (in hexane at 60° C.) contains nickel in an amount of 1,500–2,000 ppm, which represents a high content of heavy metal. Accordingly, in a number of areas of application, this product must undergo subsequent purification which is costly and entails product losses.

Another carbonyl-free nickel catalyst for cyclotrimerization of 3-methyl-1-butyne-3-ol is described in Ger. OS 36 33 033. The yields achievable with that catalyst (c. 60% of theoretical) are approximately the same as those observed with $(Bu_3P)_2NiBr_2$, but the catalytic activity with the latter system is greater than the catalytic activity according to Ger. OS 36 33 033. The mixture of nickel phosphite complexes which can be produced from nickel tetrakis(triphenyl phosphite) and an excess of sterically hindered triaryl phosphites according to said OS is preferably employed at 50°–100° C.

The above-described catalysts not only have major differences in catalytic activity, but frequently, even when their structures are similar, have widely differing selectivities in forming open chain and/or cyclic oligomers and in their degrees of oligomerization of the alkynes. As mentioned supra, most oligomerizations of 3-methyl-1-butyne-3-ol are carried out in the presence of nickel complexes (see, e.g., Jolly, P. W., in Wilkinson, G., and Stone, F. G. A., Eds., "Comprehensive Organometallic Chemistry", Vol. 8, 1982, pub. Pergamon Press, pp. 649 ff.); however, compounds of cobalt (*J. Chem. Soc. C*, 1967, 836), rhodium (*J. Organomet. Chem.*, 240, 1982, 17), and palladium (*Zh. Org. Khim.*, 19, 1983, 1853; *J. Mol. Cat.*, 26, 1984, 363) have also been tested. With some of these catalysts the addition of reducing agents led to increased activity.

To date there has not been a persuasive explanation of why nickel shows particular catalytic activity in suitable ligand fields, and why under such circumstances the proportion of cyclic oligomers formed is often high. More recent publications (see *J. Organomet. Chem.*, 258, 1983, 235; *J. Mol. Catal.*, 48, 1988, 81) deal with the effect of electronic and steric factors of widely differing classes of phosphorus-containing ligands on the activity and selectivity of nickel-containing catalysts in the cyclooligomerization of 3-methyl-1-butyne-3-ol. E. Ger. Pats. 253,024 and 263,979 show ways of selective cyclotetramerization of propargyl alcohol and other 3-hydroxy-1-alkynes with the use of highly active catalysts, where nickel-containing precatalysts react with organylation agents or reducing agents, in specific molar ratios, and the cyclooligomerizations can be carried out at 50°-110° C. It is still unclear why only cyclotetramers are produced and why one cannot even detect traces of the homologous cyclic trimers with $^1$H-NMR spectroscopy. The results do indicate how difficult it has been heretofore to predict attainable selectivity and to influence the course of the reaction in a desired manner.

In addition to the often unsatisfactory selectivity toward formation of specific oligomers, the methods according to the state of the art in the production of cyclic trimers of 3-methyl-1-butyne-3-ol and other 3-hydroxy-1-alkynes have the following drawbacks:

relatively low catalyst activity, the need to use relatively large amounts of toxic and-/or costly precatalyst stages, the need to satisfactorily dispose of corresponding amounts of the deactivated catalysts, and the difficulty in controlling the exothermic cyclooligomerizations in the presence of catalysts which frequently require a relatively long formation or incubation stage.

OBJECTS OF THE INVENTION

Accordingly, the underlying problem this invention solves is to provide catalysts with markedly higher activity and selectivity than prior art catalysts for the production of cyclooligomers like, e.g., 1,3,5-tris(α-hydroxyisopropyl)-benzene, which catalysts are usable in relatively low quantities, do not require a formation or incubation stage of indeterminate duration, and which produce the desired cyclooligomeric products (1,3,5-tris-(α-hydroxyisopropyl)-benzene or its analogues for example) with minimal amounts of impurities (e.g., a 1,2,4 cyclic trimer isomer) and substantially reduced nickel content.

Another object of the present invention is to provide a method of cyclooligomerization of 3-hydroxy-1-alkynes having 4-20 carbon atoms. These objects have been accomplished in an economical fashion whereby 3-methyl-1-butyne-3-ol and/or other 3-hydroxy-1-alkynes are cyclooligomerized in a suitable diluent agent, preferably methyl tert-butyl ether (MTBE), in the presence of a homogeneous phosphite- and nickel-containing catalyst formed from a nickel compound soluble in the reaction medium,
a phosphite of an ortho-substituted phenol, and
an organometallic alkylating agent.

wherein the catalyst may optionally be formed in the presence of an unconjugated diene and, optionally, a small amount of the reactant 3-hydroxy-1-alkyne, to yield a particularly active catalyst.

More particularly, a method of cyclooligomerization of 3-hydroxy-1-alkynes having 4-20 C atoms is provided, particularly cyclooligomerization of 3-methyl-1-butyne-3-ol to yield 1,3,5-tris(α-hydroxyisopropyl)-benzene, with the aid of nickel-containing catalysts characterized in that the catalysts are formed from 1) a nickel compound soluble in the reaction medium, 2) a phosphite of an ortho-substituted phenol, and 3) an organoaluminum compound of formula

where
R represents a branched or unbranched $C_1$-$C_{20}$, particularly a $C_1$-$C_4$, alkyl group.
X represents hydrogen or chlorine, and
n = 0 or 1, or a $C_1$-$C_{20}$ (preferably $C_1$-$C_4$) alkyllithium or a $C_1$-$C_{20}$ (preferably $C_1$-$C_4$) alkylmagnesium compound, in the presence of an aprotic diluent or solvent,
optionally an unconjugated diene, and
optionally an amount of between 0 and 100 mol of the reactant 3-hydroxy-1-alkyne being cyclooligomerized per mol of the nickel compound, wherein said catalyst formation is carried out at 0°-50° C. (with effective intermediate temperatures of 10, 20, 30 and 40° C.), and the cyclooligomerization of the reactant 3-hydroxy-1-alkynes added to the catalyst is carried out at a temperature of from 0°-80° C. (with effective intermediate temperatures of 10°, 20°, 30°, 40°, 50°, 60°and 70° C.), preferably between 30°14 50° C., and the diluent or solvent is added in amounts of >200 parts by weight (pbw) per 100 pbw of the 3-hydroxy-1-alkyne, up to 1000 or 10,000 pbw of diluent or solvent per 100 pbw of alkyne with effective intermediate amounts being 300, 400, 500, 600, 700, 800, 900, 1500, 2000, 3000, 4000, 5000, 6000, 7000, 8000, and 9000 pbw of solvent or diluent per 100 pbw of alkyne.

It has surprisingly been found that only when the above-stated reaction scheme is adhered to a nickel-containing carbonyl-free catalyst system is obtained which has high activity and which can be employed in small amounts to catalyze the conversion of 3-methyl-1-butyne-3-ol (and other 3-hydroxy-1-alkynes with 4°-20 C atoms) to 1,3,5-tris(α-hydroxyisopropyl)benzene (and corresponding 1,3,5-cyclooligomers), particularly in MTBE, with high selectivity and with lower nickel contents in the cyclooligomeric products than products prepared according to the methods of the existing state of the art.

The use of phosphites as components of nickel-containing catalysts is known, as mentioned supra (see, e.g., Ger. Pats. 1,159,951, 2,046,200, 2,056,555, and 3,633,033; and *J. Organomet. Chem.*, 258, 1983, 235); but the preparation and/or use of these catalysts is accompanied by one or more of the above-mentioned drawbacks. Also mentioned is the favorable influence of tris(2-tert-butylphenyl)- and tris(2,6-dimethylphenyl) phosphite and similar phosphite ligands in the thereby modified nickel bis(1,5-cyclooctadiene) complexes on selectivity in the formation of 1,3,5-tris(α-hydroxyisopropyl)-benzene from 3-methyl-1-butyne-3-ol (see *J. Organomet. Chem.*, 258, 1983, 235). Here, cyclooligomerizations were carried out with small amounts of alkyne. Catalysts produced from Ni(COD)$_2$, which is sensitive to air and moisture, had relatively low activity, and consequently are deemed essentially unusable in an industrial method.

In the light of the above-described drawbacks of the methods according to the state of the art, it could not be foreseen that the problems associated with these methods could be remedied by the choice of certain method features relating to the production and composition of the catalyst and the method of cyclotrimerizing 3-methyl-1-butyne-3-ol in aprotic diluents (preferably MTBE). However, the combination of the above-described measures, with observance of all the prescribed conditions, led to success, enabling the synthesis of 1,3,5-tris(α-hydroxyisopropyl)-benzene and cyclooligomers of various other 3-methyl-1-alkynes, wherein the cyclooligomeric products contain substantially less of the 1,2,4-isomers (and analogous impurities), and less nickel than prior art methods. The presence of the inventive diluent, preferably MTBE, facilitates dissipation of the heat of reaction which is liberated, thereby allowing rapid introduction of the 3-hydroxy-1-alkyne which is to be cyclooligomerized; i.e., the cyclooligomerization can be carried out at improved yields per unit space per unit time, and therefore more economically. Finally, because of the small amount of catalyst used, when the catalyst becomes deactivated, by hydrolysis or otherwise, the disposal problem presented is only a fraction of that characteristically presented by the methods according to the existing state of the art.

According to the inventive method, 1,3,5-tris-(α-hydroxyisopropyl)-benzene or the cyclooligomerization product of a 3-hydroxy-1-alkyne can be manufactured as follows:

a) The oligomerization catalysts are prepared from a nickel compound soluble in the reaction medium, in the presence of a phosphite of an ortho-substituted phenol,
an aprotic diluent,
optionally an unconjugated diene, and
optionally a portion of the 3-hydroxy-1-alkyne being cyclooligomerized, at 0°–50° C., by addition of organoaluminum compounds of formula $$AlR_{(3-n)}X_n.$$

where
R represents $C_1$–$C_{20}$ alkyl,
X represents hydrogen or chlorine, and
n = 0 or 1, or by addition of $C_1$–$C_{20}$ alkyllithium or $C_1$–$C_{20}$ alkylmagnesium compounds, wherein the molar ratio of the nickel compound, the phosphite, the unconjugated diene, and the organoaluminum (or alkyllithium or alkylmagnesium) component may vary within the range 1:(0.5–4):(1–3):(1–5), respectively wherein a preferred range is 1:(1–2):(1.5–2.5):(1.5–2.5) respectively;

b) The catalyst is employed in amounts of 0.01–2 mol%, preferably 0.02–0.2 mol% (based on the molar amount of 3-methyl-1-butyne-3-ol or 3-hydroxy-1-alkyne employed);

c) The cyclooligomerization is carried out at temperatures of 0°–80° C., preferably 30°–50° C.; and d) The diluents to be used are employed in amounts of more than 200 pbw, preferably more than 300 pbw, per 100 pbw 3-methyl-1-butyne-3-ol or 3-hydroxy-1-alkyne. The amount of the diluents is increased when larger amounts of catalyst are employed.

Candidates for use as soluble nickel compounds for preparing the catalyst are nickel(II) salts of long chain ($C_4$–$C_{22}$) carboxylic acid, e.g., nickel(II) octoate or stearate, but above all particular compounds such as nickel(II) acetylacetonate ("Ni(acac)$_2$"). For complexing the central nickel atom, phosphites of ortho-substituted phenols of general formula P(OR)$_3$ are used where R is an ortho linear or branched $C_1$–$C_6$ alkyl or phenyl substituted phenyl radical with optional additional $C_1$–$C_6$ alkyl or phenyl ring substituents; preferred ar tris(2-tert-butylphenyl)- and particularly tris(2,6-dimethylphenyl) phosphite.

$C_5$–$C_{10}$ linear and cyclo unconjugated dienes like 1,5-cyclooctadiene, 1,5-hexadiene, and 1,4-pentadiene, and similar compounds, are used as unconjugated dienes; preferred is 1,5-cyclooctadiene, which is inexpensive and is available in large quantities.

As diluents, saturated aliphatic or cycloaliphatic $C_5$–$C_{25}$ hydrocarbons may be used, e.g. hexane, cyclohexane, ethylcyclohexane, isopropylcyclohexane (hydrocumene), or decalin. Aromatic and araliphatic $C_6$–$C_{25}$ hydrocarbons may also be used, such as benzene, toluene, or xylene, but above all ethers which do not form complexes, or form complexes only weakly, such as the preferred MTBE.

The diluents, the 3-hydroxy-1-alkynes which are to undergo reaction and the catalyst components should all be substantially free of water and catalyst poisons. Catalyst formation (with addition of organoaluminum compounds, etc.) should be carried out under an inert gas atmosphere.

The cyclooligomers of 3-hydroxy-1-alkynes which can be produced according to the inventive method are useful intermediates in the production of valuable products, such as products in the area of trisphenols which can be produced by condensation of the cyclooligomers with phenols. Also, 1,3,5-tris(α-hydroxyisopropyl)-benzene, which is an intermediate in the production of phloroglucinol via 1,3,5-tris(α-hydroperoxyisopropyl)-benzene, can be produced from 3-methyl-1-butyne-3-ol in better yields, with better selectivity, and in higher purity.

The inventive method will be described in more detail by means of the following Examples which illustrate the present invention, not limit it:

EXAMPLES

The cyclooligomerizations were carried out in 250–2,000 ml multi-necked flasks each equipped with a stirrer, an internal thermometer, an inert gas inlet tube, and a dropping funnel with pressure equalization. All glass parts were dried at ≦135° C. prior to use.

The component solutions for preparing the catalyst were prepared and stored under dried inert gas, under conditions of exclusion of moisture. The 3-methyl-1-butyne-3-ol (3-MB) was purified by distillation under reduced pressure (boiling point 60° C. at 100 hPa); the small forerun was discarded. The residual water content was determined by Karl Fischer titration. Any moisture which might be present in the nickel(II) acetylacetonate (Ni(acac)$_2$) was removed by azeotropic distillation with toluene.

Tris(2,6-dimethylphenyl) phosphite can be produced from PCl$_2$ and 2,6-dimethylphenol, with recrystallization from cyclohexane.

Any (hydro)peroxides present in the 1,5-cyclooctadiene (and other unconjugated, transition metal chelating dienes) can be removed by percolation over Al$_2$O$_3$ in an inert gas atmosphere. The solvents (such as cyclohexane, toluene, or MTBE) were dried over molecular sieves.

In all of the cyclooligomerizations represented in the following Examples, first the solvent was charged, and then the prescribed amounts of nickel compound, phosphite ligand, and (if any) 1,5-cyclooctadiene and/or the small initial amount of 3-methyl-1-butyne-3-ol were added, at room temperature, following which in general the mixture was cooled to 0°–5° C., and finally the catalyst formation was carried out by addition of the organoaluminum component. The subsequent cyclooligomerization of the 3-hydroxy-1-alkyne was carried out with thorough mixing of the reaction mixture and with slow dropwise addition of the (remaining) 3-methyl-1-butyne-3-ol, in order to ensure dissipation of the heat of reaction liberated, and thus to ensure that the reaction temperature was maintained constant. After completion of the addition of the 3-hydroxy-1-alkyne to the reaction mixture, the reaction was continued for approximately 4-6 hr at the same temperature, followed by approximately 16 hr at room temperature, to complete the conversion. Then the catalyst was deactivated with a few drops of water or dilute acid. The precipitate which formed during the cyclooligomerization of 3-methyl-1-butyne-3-ol was filtered out, washed with a small amount of solvent, dried, and subjected to analysis. In the case of soluble cyclooligomers, they were subjected to isolation and analysis. The amount of the various oligomers and isomers were determined by gas chromatography.

To determine the nickel content, the oligomers were decomposed and the nickel content of the residue was determined.

Example I (Comparative Example A)

In a 250 ml three-necked flask in an inert gas atmosphere, 42.3 g (0.5 mol) 3-methyl-1-butyne-3-ol (3-MB) and 1.6 g (2.55 mmol) bis(tri-(n-butyl) phosphine) nickel dibromide were dissolved in 50 ml hexane, and the mixture was heated to 60° C. After stirring c. 2 hr at this temperature, a beige-colored solid began to precipitate, with liberation of heat of reaction. After 5 hr the reaction was terminated, the reaction mixture was cooled, and the precipitate which had formed was filtered out. After washing with ether and drying, a sand-colored solid was isolated which was recrystallized from relatively large amounts of toluene.

The yield was 24 g (56.7% of theoretical). Melting point was 148°-150° C. Nickel content was 2,000 ppm. Ratio of 1,3,5- to 1,2,4-tris(α-hydroxyisopropyl)-benzene Was 92.6% : 7.4%.

Example 2 (Comparative Example B)

In a 250 ml three-necked flask 10 ml of a 1.25 mol/L solution of nickel(II) acetylacetonate in toluene was dissolved in a mixture of 8.5 g (0.1 mol) 3-methyl-1-butyne-3-ol and 50 ml cyclohexane. Under stirring, 0.3 mmol triethylaluminum was added at 5° C., following which an additional 34 g 3-methyl-1-butyne-3-ol was added dropwise to the dark solution, at 50° C. After reaction 3 hr, the catalyst was decomposed and the product mixture was analyzed by gas chromatography. The amount of 3-MB cyclic trimers among the numerous compounds formed was <5%. The 1,2,4- and 1,3,5-isomers were obtained in the ratio 55 : 45. This Example demonstrates that cyclic trimers of 3-MB are produced to a relatively low degree in the absence of phosphorus-containing ligands.

Examples 3-11 (Table I)

100 ml toluene containing 1.25 mmol nickel(II) acetylacetonate, the respective phosphite, and triethylaluminum, in the amounts shown in Table I, where L1 = tris(2-tert-butylphenyl) phosphite,
L2 = tris(2,4-di-tert-butylphenyl) phosphite,
L3 = tris(2-phenylphenyl) phosphite, and
L4 = tris(2,6-dimethylphenyl) phosphite, were charged to a 250 ml three-necked flask, at 40°-50° C. Then a total of 25 ml (260 mmol) 3-MB was added dropwise at a rate such that the reaction temperature was maintained nearly constant. For this purpose, first 3-5 ml was added, and the remainder was withheld until the catalyst forming step—requiring 20-45 min and recognizable by a color change and an exothermic reaction—was concluded.

After the time indicated in Table I (5-6.5 hr), the reactions were terminated by deactivation of the catalyst, and the precipitate was analyzed.

The Examples all demonstrate excellent results and show that in the presence of ligands L1 and L4, catalysts with higher activity are formed, whereby 1,3,5-tris(α-hydroxyisopropyl)-benzene was produced with higher selectivity.

Examples 12-23 (see Table II)

In the manner described above (see Examples 3-11), 25 mol 3-MB was cyclooligomerized at temperatures between 20° and 80° C. in the presence of various diluents.

The test results reveal that the present carbonyl-free nickel catalyst system can be used in various diluents, wherewith particularly pure raw products are obtained in MTBE; and that the addition of 1,5-cyclooctadiene leads to particularly active catalysts which produce high yields of the cyclic trimers at a high rate of transformation.

Examples 24-33 (see Table III)

In the manner employed in Examples 3-11, 25 ml (c. 260 mmol) 3-MB was reacted in the presence of nickel catalysts containing tris(2,6-dimethylphenyl) phosphite and (except in Ex. 24) 1,5-cyclooctadiene, which catalysts had been activated by addition of small amounts of triethylaluminum and/or diisobutylaluminum hydride.

The amounts of precipitate (of 1,3,5-tris(α-hydroxyisopropyl)-benzene) observed to be formed after various intervals of time indicate that 1,5-cyclooctadiene is an advantageous co-catalyst, that the cyclooligomerization is most rapid at 50° C. among the temperatures employed (Table II), and that the catalytic activity of the nickel-containing system also depends on the amount of the organoaluminum compounds, where an optimum, which depends on the ratios of all of the catalyst components used, can be determined in each case. It can also be seen that cyclohexane dissolves the 3-MB cyclic trimer more poorly than others.

Examples 34-40 (see Table IV)

In the manner described in Examples 3-11, 100 ml (c. 1,040 mmol) 3-MB was reacted, in a 2,000 ml three-necked flask, with the use of diisobutylaluminum hydride or triethylaluminum as components of the nickel-containing carbonyl-free cyclooligomerization catalysts, in MTBE.

The Examples indicate that the cyclooligomerization can be carried out with less catalyst charged than according to the existing state of the art, and that in the process of the invention the raw products obtained are very pure, having only a fraction of the nickel content observed otherwise (cf. Example 1).

Examples 41-48 (see Table V)

In the manner described in Examples 3-11, 25 ml (c.260 mmol) 3-MB was cyclooligomerized at 50° C. in the presence of a catalyst system formed at 5° C. or 50° C. from nickel(II) acetylacetonate, tris(2,6-dimethylphenyl) phosphite, triethylaluminum, and optionally 1,5-cyclooctadiene.

The Examples indicate that generally low nickel contents are found in the isolated raw products, and that these results are obtained even when the catalyst composition is varied. The addition of co-catalyst non-conjugated diene always leads to higher yields, independently of the temperature of catalyst formation.

Examples 49–52 (see Table VI)

In a manner analogous to that of Examples 3–11, 400 ml 3-MB dissolved in 1,200 ml MTBE was oligomerized, in a 2,000 ml threenecked flask. Catalyst formation was carried out at 5° C. in the presence of $AlR_3$ where It is seen that the 3-hydroxy-1-alkyne is cyclotrimerized even when very small amounts of catalyst are employed.

While the present invention has been described in terms of its specific embodiments, certain modifications and equivalents will be apparent to those skilled in the art and are intended to be included within the scope of the present invention, which is to be limited only by the scope of the appended claims.

TABLE I

Oligomerization of 3-methyl-1-butyne-3-ol in the presence of phosphite-modified nickel-containing catalysts, in toluene.

| Example No. | Phosphite Ligand | Amount of Diluent (ml) | Catalyst (ratios are in molar units) Ni(acac)$_2$ [mmol] | Mol ratio Ni:L$_x$: Al(C$_2$H$_5$)$_3$ | Reaction Temp. (°C.) | Reaction Time (hr) | Yield (g) | Yield (% of theoretical) | Proportion of cyclic trimers (%, determined by Gc) 1,3,5-tris(α-hydroxy-isopropyl)-benzene | 1,2,4-tris(α-hydroxy-isopropyl)-benzene | Ratio of 1,3,5-isomer to 1,2,4 isomer | Melting Range (°C.) |
|---|---|---|---|---|---|---|---|---|---|---|---|---|
| 3 | L$_1$ | 100 | 1.25 | 1:2:1.6 | 50 | 5.5 | 20.1 | 93.4 | 83.0 | 1.2 | 98.6/1.4 | 149–153 |
| 4 | L$_1$ | 100 | 1.25 | 1:2:2.3 | 20 | 6 | 16.0 | 74 | 88.4 | 0.7 | 99.2/0.8 | 154–155 |
| 5 | L$_1$ | 100 | 1.25 | 1:2:4.5 | 20 | 5.5 | 12.3 | 57 | 82.2 | 0.8 | 99.0/1.0 | 152–154 |
| 6 | L$_2$ | 100 | 1.25 | 1:2:2.4 | 50 | 5.5 | 12.3 | 57 | 84.5 | 0.4 | 99.5/0.5 | 152–153 |
| 7 | L$_3$ | 100 | 1.25 | 1:2:1.2 | 50 | 5 | 12.1 | 56.2 | 84.0 | 7.5 | 91.8/8.2 | 151–153 |
| 8 | L$_3$ | 100 | 1.25 | 1:3:2.4 | 50 | 6.5 | 17.1 | 79.5 | 81.5 | 6.2 | 92.9/7.1 | 150–153 |
| 9 | L$_4$ | 150 | 1.25 | 1:2:1.6 | 50 | 4.5 | 19.3 | 90.2 | 90.6 | 1.1 | 98.8/1.2 | 150–152 |
| 10 | L$_4$ | 150 | 1.25 | 1:3:1.6 | 50 | 5.5 | 19.5 | 90.6 | 89.5 | 1.2 | 98.7/1.3 | 150–153 |
| 11 | L$_4$ | 150 | 1.25 | 1:3:2.4 | 50 | 5.0 | 19.1 | 88.7 | 85.1 | 1.5 | 98.3/1.7 | 150–152 |

All reactions were carried out in toluene, with 25 ml (260 mmol) of 3-MB, and with a Mol ratio of 3-MB to Ni of 200:1
Catalyst formation was conducted at 40–50° C.

TABLE II

Oligomerization of 3-methyl-1-butyne-3-ol with phosphite-modified nickel-containing catalysts, in various diluents, with variations in reaction temperature and catalyst composition

| Example No. | Amount of Type | Amount (ml) | Catalyst (ratios are in molar units) Ni(acac)$_2$ (mmol) | Ni:L$_x$:L$_5$ Al(C$_2$H$_5$)$_3$ | Reaction Temp. (°C.) | Reaction Time (hr) | Yield (grams) | Oligomer of 3-methyl-1-butyne-3-ol (raw product) Yield (% of theoretical) | Proportion of cyclic trimers (%, determined by GC) 1,3,5-tris (α-hydroxy isopropyl)-benzene | 1,2,4-tris (α-hydroxy isopropyl)-benzene | Melting range (°C.) |
|---|---|---|---|---|---|---|---|---|---|---|---|
| A) Tests with addition of ligand L$_1$ (which is tris(2-tert-butylphenyl) phosphite), and with addition of L$_5$ (which is 1,5-cyclooctadiene). | | | | | | | | | | | |
| 12 | Cyclohexane | 175 | 1.25 | 1:2:2:2.25 (L$_1$) | 50 | 7 | 15.4 | 71.6 | 73.9 | 0.7 | 151–153 |
| 13 | MTBE | 175 | 1.25 | 1:2:2:2.25 (L$_1$) | 50 | 7 | 14.8 | 68.7 | 77.3 | | 157–158 |
| B) Tests with addition of ligand L$_4$ (which is tris(2,6-dimethylphenyl) phosphite), as well as (in some cases) L$_6$. | | | | | | | | | | | |
| 14 | Toluene | 150 | 1.25 | 1:2:0:2.25 L$_4$) | 50 | 5.5 | 20.0 | 92.9 | 84.8 | 1.7 | 152–154 |
| 15 | Toluene | 150 | 1.25 | 1:2:0:2.25 L$_4$) | 80 | 5.5 | 18.4 | 85.5 | | | 152–155 |
| 16 | Toluene | 150 | 1.25 | 1:2:0:4.5 | 50 | 5.5 | 16.2 | 75.2 | 84.8 | 2.4 | 151–153 |
| 17 | Toluene | 100 | 1.25 | 1:2:0:2.25 | 20 | 5.5 | 18.0 | 83.7 | 88.7 | 1.4 | 153–155 |
| 18 | Toluene | 100 | 1.25 | 1:2:1.5:2.26 | 20 | 5.5 | 20.6 | 95.0 | 88.3 | 1.3 | 152–154 |
| 19 | Cyclohexane | 175 | 1.25 | 1:2:0:2.25 | 50 | 2.5 | 15.4 | 71.6 | 86.8 | 1.3 | 151–154 |
| 20 | Cyclohexane | 175 | 1.25 | 1:2:2:2.25 | 50 | 1 | 18.8 | 87.3 | 84.6 | 1.6 | 149–152 |
| 21 | Cyclohexane | 175 | 1.25 | 1:2:2:2.25 | 50 | 2.5 | 20.1 | 93.3 | 84.4 | 1.7 | 148–152.5 |
| 22 | Cyclohexane | 175 | 1.25 | 1:1:2:2.25 | 50 | 2.5 | 19.2 | 89.5 | 84.0 | 1.7 | 148–153 |
| 23 | Cyclohexane | 175 | 1.25 | 1:4:2:2.25 | 50 | 2.5 | 19.7 | 91.6 | 84.8 | 1.2 | 149–153 |

R is ethyl.

TABLE III

Oligomerization of 3-methyl-1-butyne-3-ol with catalysts containing tris(2,6-dimethylphenyl) phosphite, with variations in the organometallic compound, the type and amount of the diluent, the reaction temperature, and the amount of catalyst

| Example No. | Diluent Type of Diluent | Diluent Amount of Diluent [ml] | Catalyst (ratios are in molar units) Ni(acac)$_2$ [mmol] | Ni:L$_4$: L$_5$:AlR$_2$X | Molar ratio of 3-MB to Ni | Reaction temperature (°C.) | time [h] |
|---|---|---|---|---|---|---|---|
| A) Tests with use of triethylaluminum and 25 ml (260 mmol) 3-MB | | | | | | | |
| 24 | MTBE | 175 | 1.28 | 1:2:0:2.25 | 200 | 20 | 7 |
| 25 | " | 175 | 1.28 | 1:2:2:2.2 | 200 | 20 | 7 |

TABLE III-continued

Oligomerization of 3-methyl-1-butyne-3-ol with catalysts containing tris(2,6-dimethylphenyl) phosphite, with variations in the organometallic compound, the type and amount of the diluent, the reaction temperature, and the amount of catalyst

| Example No. | Diluent | | | | | | |
|---|---|---|---|---|---|---|---|
| 26 | " | 175 | 1.28 | 1:2:2:1.1 | 200 | 50 | 7 |
| B) Tests with use of diisobutylaluminum hydride and 25 ml (260 mmol) 3-MB | | | | | | | |
| 27 | Cyclo-hexane | 175 | 1.28 | 1:2:2:2.25 | 200 | 50 | 2.5 |
| 28 | MTBE | 175 | 1.28 | 1:2:2:2.25 | 200 | 50 | 6 |
| 29 | " | 175 | 1.28 | 1:2:2:1.1 | 200 | 50 | 7 |
| 30 | " | 175 | 1.28 | 1:2:2:2.25 | 200 | 30 | 7 |
| 31 | " | 175 | 1.28 | 1:2:2:1.1 | 200 | 30 | 7 |
| 32 | " | 175 | 1.28 | 1:2:2:2.25 | 200 | 20 | 6.5 |
| 33 | " | 175 | 1.28 | 1:2:2:1.1 | 200 | 20 | 6.5 |

| Example No. | Reaction time after which a precipitate formed (min) | Yield grams | Yield (% of theoretical) | 1,3,5-tris($\alpha$-hydroxy-isopropyl)-benzene | Proportion of cyclic trimers (%, determined by GC) 1,2,4-tris($\alpha$-hydroxy-isopropyl)-benzene | Melting range °C |
|---|---|---|---|---|---|---|
| A) Tests with use of triethylaluminum and 25 ml (260 mmol) 3-MB | | | | | | |
| 24 | 90 | 15 | 70 | 96.6 | 0.6 | 157.0–158.0 |
| 25 | 75 | 16.1 | 75 | 97.3 | 0.6 | 157.0–157.5 |
| 26 | 30 | 16.5 | 76.8 | 97.5 | | 157.0–157.5 |
| B) Tests with use of diisobutylaluminum hydride and 25 ml (260 mmol) 3-MB | | | | | | |
| 27 | 5 | 19.2 | 89 | 83.3 | 1.5 | 150.0–153.0 |
| 28 | 23 | 16.5 | 76.7 | 97.8 | | 157.0–158.0 |
| 29 | 25 | 15.9 | 74.1 | 98.4 | 0.2 | 157.0–158.0 |
| 30 | 45 | 14.3 | 66.7 | 98.1 | 0.3 | 156.5–157.0 |
| 31 | 75 | 10.1 | 46.9 | 98.8 | 0.15 | 157.5–158.0 |
| 32 | 75 | 15.3 | 71.1 | 96.7 | 0.6 | 157.5–158.0 |
| 33 | 150 | 8 | 37.3 | 98.3 | 0.5 | 157.5–158.5 |

TABLE IV

Oligomerization of 3-methyl-1-butyne-3-ol with catalysts containing tris(2,6-dimethylphenyl) phosphite, in MTBE, with variations in the organoaluminum co-catalyst.

| Example No. | Amount of MTBE [ml] | Catalyst (ratios are in molar units) Ni(acac)$_2$ [mmol] | Ni:L$_4$: L$_5$:AlR$_2$X | Molar ratio of 3-MB to Ni | Reaction Temp. [°C] | Reaction Time [hr] | Reaction time after which a precipitate formed [min] |
|---|---|---|---|---|---|---|---|
| A) Tests with use of diisobutylaluminum hydride and 100 ml (1040 mmol) 3-MB. | | | | | | | |
| 34 | 700 | 2.50 | 1:2:2:2.25 | 400 | 50 | 7 | 60 |
| B) Tests with use of triethylaluminum and 100 ml (1040 mmol) 3-MB. | | | | | | | |
| 35 | 700 | 2.56 | 1:2:2:2.25 | 400 | 50 | 7 | 45 |
| 36 | 700 | 1.28 | 1:2:2:2.25 | 800 | 50 | 7 | 50 |
| 37 | 450 | 1.28 | 1:2:2:2.25 | 800 | 50 | 7 | 35 |
| 38 | 300 | 1.28 | 1:2:2:2.25 | 800 | 50 | 7 | 35 |
| 39 | 700 | 1.28 | 1:2:2:2.25 | 800 | 30 | 7 | 95 |
| 40 | 300 | 0.84 | 1:2:2:2.4 | 1200 | 50 | 7 | 75 |

| Example No. | Yield [gram] | Yield [% of theoretical] | 1,3,5-tris($\alpha$-hydroxy-isopropyl)-benzene | Proportion of cyclic trimers (% determined by GC) 1,2,4-tris($\alpha$-hydroxy-isopropyl)-benzene | Melting Range [°C] | Nickel content [ppm] |
|---|---|---|---|---|---|---|
| A) Tests with use of diisobutylaluminum hydride and 100 ml (1040 mmol) 3-MB. | | | | | | |
| 34 | 57.7 | 67.1 | 98.3 | 0.06 | 158.0–159.0 | 290 |
| B) Tests with use of triethylaluminum and 100 ml (1040 mmol) 3-MB. | | | | | | |
| 35 | 66.4 | 77.2 | 95.5 | 0.3 | 157.5–158.5 | 270 |
| 36 | 54 | 62.3 | 96.8 | 0.25 | 157.0–158.0 | 130 |
| 37 | 65.5 | 76.1 | 96.0 | 0.4 | 157.5–158.5 | 160 |
| 38 | 63.2 | 73.5 | 97.6 | 0.2 | 156.5–157.5 | 240 |
| 39 | 56.8 | 66 | 97.6 | 0.45 | 157.5–158.5 | 160 |
| 40 | 64.7 | 75.2 | 95.6 | 0.4 | 157.0–158.0 | 90 |

TABLE V

Oligomerization of 3-methyl-1-butyne-3-ol -- effect of catalyst formation on the catalyst activity, and on the nickel content in the 1,3,5-tris($\alpha$-hydroxyisopropyl)benzene

| Example No. | Amount of 3-MB in starting mixture [ml] | Amount of MTBE solvent in starting mixture (MTB) | Catalyst (ratios are in molar units)* Ni:L$_4$:L$_5$: Al(C$_2$H$_5$)$_3$ | Temperature of Catalyst formation | Molar ratio of 3-MB to Ni | Reaction Temp. [°C] | Reaction Time [hr] |
|---|---|---|---|---|---|---|---|
| 41 | 25 | 100 | 1:2:0:2.2 | 50 | 400 | 50 | 7 |

TABLE V-continued

Oligomerization of 3-methyl-1-butyne-3-ol -- effect of catalyst formation on the catalyst activity, and on the nickel content in the 1,3,5-tris(α-hydroxyisopropyl)benzene

| | | | | | | | |
|---|---|---|---|---|---|---|---|
| 42 | 25 (= 260 mmol) | " | 1:2:0:2.2 | 5 | 400 | 50 | 7 |
| 43 | 25 (= 260 mmol) | " | 1:2:2:2.2 | 50 | 400 | 50 | 7 |
| 44 | 25 (= 260 mmol) | " | 1:2:2:2.2 | 5 | 400 | 50 | 7 |
| 45 | 25 (= 260 mmol) | " | 1:4:2:2.2 | 50 | 400 | 50 | 7 |
| 46 | 25 (= 260 mmol) | " | 1:4:2:2.2 | 5 | 400 | 50 | 7 |
| 47 | 25 (= 260 mmol) | " | 1:2:2:3.1 | 50 | 400 | 50 | 7 |
| 48 | 25 (= 260 mmol) | " | 1:2:2:3.1 | 5 | 400 | 50 | 7 |

| Example No. | Yield [gram] | [% of theoretical] | Proportion of cyclic trimers (% determined by GC) 1,3,5-tris(α-hydroxy-isopropyl)benzene | 1,2,4-tris(α-hydroxy-isopropyl)benzene | Melting Range [°C.] | Nickel content [ppm] |
|---|---|---|---|---|---|---|
| 41 | 12.9 | 60 | 97.0 | 0.15 | 159.0–159.8 | 210 |
| 42 | 5.2 | 24.4 | | | 159.9–160.0 | |
| 43 | 15.9 | 74.2 | 97.0 | 0.25 | 158.6–159.3 | 190 |
| 44 | 15.8 | 73.6 | 97.2 | 0.2 | 158.4–159.2 | 130 |
| 45 | 16.3 | 75.7 | 97.9 | 0.2 | 158.2–159.5 | 210 |
| 46 | 16.5 | 76.9 | 98.2 | 0.2 | 158.4–159.5 | 230 |
| 47 | 15.6 | 72.7 | 96.7 | 0.3 | 158.2–158.6 | 500 |
| 48 | 15.6 | 72.7 | 96.9 | 0.3 | 158.0–158.8 | 430 |

*All tests were done with 0,65 mmol Ni(acac)$_2$

TABLE VI

Oligomerization of 3-methyl-1-butyne-3-ol-benzene -- variation of amount of catalyst.

| Example No. | Amount of 3-MB in starting mixture [ml] | Amount of MTBE solvent in starting mixture (MTB) | Ni(acac)$_2$ [mmol] | Catalyst (ratios are in molar units) Ni:L$_4$:L$_5$:AlR$_3$ | Temperature of Catalyst formation [°C.] | Molar ratio of 3-MB to Ni | Reaction Temp [°C.] | Time [hr] |
|---|---|---|---|---|---|---|---|---|
| 49 | 400 | 1200 | 3.4 | 1:2:2:2.4 | 5 | 1200 | 50 | 7 |
| 50 | 400 | 1200 | 2.25 | 1:2:2:2.4 | 5 | 1850 | 50 | 7 |
| 51 | 400 | 1200 | 1.7 | 1:2:2:2.4 | 5 | 2450 | 50 | 7 |
| 52 | 400 | 1200 | 1.1 | 1:2:2:2.4 | 5 | 3650 | 50 | 7 |

| Example No. | Yield [gram] | [% of theoretical] | Proportion of cyclic trimers (% determined by GC) 1,3,5-tris(α-hydroxy-isopropyl)benzene | 1,2,4-tris(α-hydroxy-isopropyl)benzene | Melting Range [°C.] | Nickel content [ppm] |
|---|---|---|---|---|---|---|
| 49 | 274.6 | 79.9 | 95.7 | 0.4 | 157.3–158.6 | 170 |
| 50 | 243.2 | 70.8 | 97.4 | 0.3 | 158.0–158.8 | 60 |
| 51 | 208.9 | 60.7 | 96.8 | 0.2 | 158.0–158.9 | 40 |
| 52 | 133.6 | 38.8 | 97.3 | 0.2 | 157.5–159.4 | 20 |

What is claimed as new and desired to be secured by Letters Patent of The United States Is:

1. A process for the cyclooligomerization of 3-methyl-1-butene-3-ol into 1,3,5-tris(α-hydroxyisopropyl)-benzene comprising the steps of:
    forming a nickel-containing catalyst solution by solubilizing a nickel compound, a phosphite of an ortho-substituted phenol and a compound selected from the group consisting of a) an organoaluminum compound of the formula AlR$_{(3-n)}$X$_n$ where R represents a C$_{1-20}$ linear or branched alkyl group, X represents hydrogen or chlorine and n=0 or 1, b) a C$_1$-C$_{40}$ alkyllithium compound and c) a C$_{1-20}$ alkylmagnesium compound
    in an aprotic diluent at between 0° and 50° C. and adding 3-methyl-1-butyne-3-ol to said catalyst solution at a temperature of from 0°–80°.

2. The process of claim 1, wherein said catalyst is formed by further adding an unconjugated diene in said aprotic diluent.

3. The process of claim 1, wherein said catalyst is formed by further adding an unconjugated diene and a fraction of the 3-methyl-1-butyne-3-ol to be cyclooligomerized in said aprotic diluent.

4. The process of claim 1, wherein said catalyst is formed by further adding a fraction of the 3-methyl-1-butyne-3-ol to be cyclooligomerized in said aprotic diluent.

5. The process of claim 1, wherein said cyclooligomerization is carried out at a temperature between 30° and 50° C.

6. The process of claim 1, wherein said diluent is present in an amount greater than 200 pbw per 100 pbw of said 3-methyl-1-butyne-3-ol.

7. The process of claim 1, wherein said phosphite of an ortho-substituted phenol is selected from the group consisting of tris(2-tert-butylphenyl)-phosphite and tris(2,6-dimethylphenyl)phosphite.

8. The process of claim 1, wherein said diluent is methyl tert-butylether.

9. The process of claim 2, wherein said unconjugated diene is 1,5-cyclooctadiene.

10. The process of claim 1, wherein said catalyst is present in solution in an amount of 0.01–2 mol% based on the molar amount of said 3-methyl-1-butyne-3-ol added.

11. The process of claim 1, wherein said catalyst is present in solution in an amount of 0.02–0.2 mol% based on the molar amount of said 3-methyl-1-butyne-3-ol added.

12. The process of claim 1, wherein the molar ratio of said nickel compound, phosphite, unconjugated diene and organoaluminum, alkylithium or alkylmagnesium compound is 1:(0.5–4):(1–3):(1–5) respectively.

13. The process of claim 1, wherein the molar ratio of said nickel compound, phosphite, unconjugated diene and organoaluminum, alkylithium or alkylmagnesium compound is 1:(1–2):(1.5–2.5):(1.5–2.5) respectively.

* * * * *